United States Patent
Beira

(10) Patent No.: US 10,646,294 B2
(45) Date of Patent: May 12, 2020

(54) REUSABLE SURGICAL INSTRUMENT FOR MINIMALLY INVASIVE PROCEDURES

(71) Applicant: DistalMotion SA, Lausanne (CH)

(72) Inventor: Ricardo Daniel Rita Beira, Lausanne (CH)

(73) Assignee: Distalmotion SA, Epalinges (CH)

( * ) Notice: Subject to any disclaimer, the term of this patent is extended or adjusted under 35 U.S.C. 154(b) by 247 days.

(21) Appl. No.: 15/536,576

(22) PCT Filed: Dec. 18, 2015

(86) PCT No.: PCT/IB2015/002512
§ 371 (c)(1),
(2) Date: Jun. 15, 2017

(87) PCT Pub. No.: WO2016/097868
PCT Pub. Date: Jun. 23, 2016

(65) Prior Publication Data
US 2018/0000550 A1    Jan. 4, 2018

Related U.S. Application Data

(60) Provisional application No. 62/094,080, filed on Dec. 19, 2014.

(51) Int. Cl.
*A61B 34/37* (2016.01)
*A61B 17/29* (2006.01)
(Continued)

(52) U.S. Cl.
CPC .............. *A61B 34/37* (2016.02); *A61B 17/29* (2013.01); *A61B 34/71* (2016.02);
(Continued)

(58) Field of Classification Search
CPC ......... A61B 46/13; A61B 17/29; A61B 34/37; A61B 34/71; A61B 2017/2901;
(Continued)

(56) References Cited

U.S. PATENT DOCUMENTS 2,764,301 A    9/1956  Goertz et al.
2,771,199 A    11/1956 Jelatis
(Continued)

FOREIGN PATENT DOCUMENTS

CN    101584594 A    11/2009
CN    101637402 A    2/2010
(Continued)

OTHER PUBLICATIONS

US 9,232,978 B2, 01/2016, Shellenberger et al. (withdrawn)
(Continued)

*Primary Examiner* — Phong Son H Dang
(74) *Attorney, Agent, or Firm* — Eversheds Sutherland (US) LLP; Christopher C. Bolten; Nicola A. Pisano

(57) ABSTRACT

Disclosed is a reusable surgical instrument (1) with an articulated end-effector (3), such as a dissector, scissor or grasper, to enhance a surgeon's performance during various surgical procedures. The longitudinal axis of the instrument is defined by a shaft (2), comprising an internal structural element (2") covered by an external tube (2'), which may be inserted through a surgical incision into the body of a patient, optionally through a trocar. The articulated end-effector (3) is mounted on the distal extremity of the shaft's internal structural element and comprises a plurality of links interconnected by a plurality of joints, whose movements are remotely actuated by the surgeon's hands. This remote actuation is accomplished via mechanical transmission (5, 6, 7), mainly composed of flexible elements, which are able to deliver motion from a set of actuation elements, placed at a proximal extremity of the shaft (2), to the instrument's articulated end-effector (3). The external tube (2') can be easily and individually detached from the shaft (2) after each procedure, so that the instrument (1) can be more effectively cleaned and sterilized.

12 Claims, 13 Drawing Sheets

(51) Int. Cl.
*A61B 34/00* (2016.01)
*A61B 90/00* (2016.01)
*A61B 34/30* (2016.01)

(52) U.S. Cl.
CPC ............ *A61B 2017/2901* (2013.01); *A61B 2017/2927* (2013.01); *A61B 2017/2948* (2013.01); *A61B 2034/305* (2016.02); *A61B 2090/0813* (2016.02)

(58) Field of Classification Search
CPC ...... A61B 2034/305; A61B 2017/2948; A61B 2017/2927; A61B 2090/0813
See application file for complete search history.

(56) References Cited

U.S. PATENT DOCUMENTS

| | | | |
|---|---|---|---|
| 2,774,488 A | 12/1956 | Goertz | |
| 2,846,084 A | 8/1958 | Goertz et al. | |
| 3,065,863 A | 11/1962 | Saunders, Jr. | |
| 3,095,096 A | 6/1963 | Chesley | |
| 3,212,651 A | 10/1965 | Specht et al. | |
| 3,261,480 A | 7/1966 | Haaker et al. | |
| 3,297,172 A | 1/1967 | Haaker et al. | |
| 3,391,801 A | 7/1968 | Haaker | |
| 3,425,569 A | 2/1969 | Haaker et al. | |
| 4,221,516 A | 9/1980 | Haaker et al. | |
| 4,756,655 A | 7/1988 | Jameson | |
| 5,147,357 A | 9/1992 | Rose et al. | |
| 5,176,352 A | 1/1993 | Braun | |
| 5,207,114 A | 5/1993 | Salisbury et al. | |
| 5,209,747 A | 5/1993 | Knoepfler | |
| 5,304,203 A | 4/1994 | El-Mallawany et al. | |
| 5,308,358 A * | 5/1994 | Bond | A61B 17/29 606/170 |
| 5,330,502 A | 7/1994 | Hassler et al. | |
| 5,368,606 A | 11/1994 | Marlow et al. | |
| 5,383,888 A | 1/1995 | Zvenyatsky et al. | |
| 5,484,435 A | 1/1996 | Fleenor et al. | |
| 5,599,151 A | 2/1997 | Daum et al. | |
| 5,603,723 A | 2/1997 | Aranyi et al. | |
| 5,631,973 A | 5/1997 | Green | |
| 5,649,956 A | 7/1997 | Jensen et al. | |
| 5,710,870 A | 1/1998 | Ohm et al. | |
| 5,716,352 A | 2/1998 | Viola et al. | |
| 5,735,874 A | 4/1998 | Measamer et al. | |
| 5,784,542 A | 7/1998 | Ohm et al. | |
| 5,797,900 A | 8/1998 | Madhani et al. | |
| 5,810,716 A | 9/1998 | Mukherjee et al. | |
| 5,810,805 A | 9/1998 | Sutcu et al. | |
| 5,828,813 A | 10/1998 | Ohm | |
| 5,908,436 A | 6/1999 | Cuschieri et al. | |
| 5,931,832 A | 8/1999 | Jensen | |
| 5,951,587 A | 9/1999 | Qureshi et al. | |
| 5,976,122 A | 11/1999 | Madhani et al. | |
| 6,026,701 A | 2/2000 | Reboulet | |
| 6,132,368 A | 10/2000 | Cooper | |
| 6,197,017 B1 | 3/2001 | Brock et al. | |
| 6,206,903 B1 | 3/2001 | Ramans | |
| 6,233,504 B1 | 5/2001 | Das et al. | |
| 6,281,651 B1 | 8/2001 | Haanpaa et al. | |
| 6,312,435 B1 * | 11/2001 | Wallace | A61B 34/70 606/130 |
| 6,331,181 B1 * | 12/2001 | Tierney | G16H 40/63 606/130 |
| 6,358,249 B1 | 3/2002 | Chen et al. | |
| 6,361,534 B1 | 3/2002 | Chen et al. | |
| 6,364,879 B1 | 4/2002 | Chen et al. | |
| 6,371,952 B1 | 4/2002 | Madhani et al. | |
| 6,394,998 B1 | 5/2002 | Wallace et al. | |
| 6,435,794 B1 | 8/2002 | Springer | |
| 6,459,926 B1 | 10/2002 | Nowlin et al. | |
| 6,491,701 B2 | 12/2002 | Tierney et al. | |
| 6,554,844 B2 | 4/2003 | Lee et al. | |
| 6,587,750 B2 | 7/2003 | Gerbi et al. | |
| 6,594,552 B1 | 7/2003 | Nowlin et al. | |
| 6,671,581 B2 | 12/2003 | Niemeyer et al. | |
| 6,699,177 B1 | 3/2004 | Wang et al. | |
| 6,786,896 B1 | 9/2004 | Madhani et al. | |
| 6,788,999 B2 | 9/2004 | Green | |
| 6,840,938 B1 * | 1/2005 | Morley | A61B 18/1445 606/51 |
| 6,850,817 B1 | 2/2005 | Green | |
| 6,852,107 B2 | 2/2005 | Wang et al. | |
| 6,879,880 B2 | 4/2005 | Nowlin et al. | |
| 6,902,560 B1 | 6/2005 | Morley et al. | |
| 6,913,613 B2 | 7/2005 | Schwarz et al. | |
| 6,951,535 B2 | 10/2005 | Ghodoussi et al. | |
| 6,991,627 B2 | 1/2006 | Madhani et al. | |
| 6,994,708 B2 | 2/2006 | Manzo | |
| 7,048,745 B2 | 5/2006 | Tierney et al. | |
| 7,083,571 B2 | 8/2006 | Wang et al. | |
| 7,090,637 B2 | 8/2006 | Danitz et al. | |
| 7,101,363 B2 | 9/2006 | Nishizawa et al. | |
| 7,204,836 B2 | 4/2007 | Wagner et al. | |
| 7,232,440 B2 | 6/2007 | Dumbauld et al. | |
| 7,241,289 B2 | 7/2007 | Braun | |
| 7,306,597 B2 | 12/2007 | Manzo | |
| 7,316,681 B2 | 1/2008 | Madhani et al. | |
| 7,338,513 B2 | 3/2008 | Lee et al. | |
| 7,364,582 B2 | 4/2008 | Lee | |
| 7,373,219 B2 | 5/2008 | Nowlin et al. | |
| 7,398,707 B2 | 7/2008 | Morley et al. | |
| 7,481,824 B2 | 1/2009 | Boudreaux et al. | |
| 7,549,998 B2 | 6/2009 | Braun | |
| 7,594,912 B2 | 9/2009 | Cooper et al. | |
| 7,608,039 B1 | 10/2009 | Todd | |
| 7,615,002 B2 | 11/2009 | Rothweiler et al. | |
| 7,615,067 B2 | 11/2009 | Lee et al. | |
| 7,674,255 B2 | 3/2010 | Braun | |
| 7,699,855 B2 | 4/2010 | Anderson et al. | |
| 7,756,036 B2 | 7/2010 | Druke et al. | |
| 7,819,894 B2 | 10/2010 | Mitsuishi et al. | |
| 7,824,401 B2 | 11/2010 | Manzo et al. | |
| 7,828,798 B2 | 11/2010 | Buysse et al. | |
| 7,833,156 B2 | 11/2010 | Williams et al. | |
| 7,890,211 B2 | 2/2011 | Green | |
| 7,914,521 B2 | 3/2011 | Wang et al. | |
| 7,976,458 B2 | 7/2011 | Stefanchik et al. | |
| 8,048,084 B2 | 11/2011 | Schneid | |
| 8,105,320 B2 | 1/2012 | Manzo | |
| 8,114,017 B2 | 2/2012 | Bacher | |
| 8,137,263 B2 | 3/2012 | Marescaux et al. | |
| 8,142,447 B2 | 3/2012 | Cooper et al. | |
| 8,224,485 B2 | 7/2012 | Unsworth | |
| 8,246,617 B2 | 8/2012 | Welt et al. | |
| 8,267,958 B2 | 9/2012 | Braun | |
| 8,287,469 B2 | 10/2012 | Stefanchik et al. | |
| 8,292,889 B2 | 10/2012 | Cunningham et al. | |
| 8,306,656 B1 | 11/2012 | Schaible et al. | |
| 8,308,738 B2 | 11/2012 | Nobis et al. | |
| 8,332,072 B1 | 12/2012 | Schaible et al. | |
| 8,336,751 B2 | 12/2012 | Scirica | |
| 8,347,754 B1 | 1/2013 | Veltri et al. | |
| 8,353,898 B2 | 1/2013 | Lutze et al. | |
| 8,357,161 B2 | 1/2013 | Mueller | |
| 8,382,742 B2 | 2/2013 | Hermann et al. | |
| 8,388,516 B2 | 3/2013 | Sholev | |
| 8,403,832 B2 | 3/2013 | Cunningham et al. | |
| 8,414,475 B2 | 4/2013 | Sholev | |
| 8,418,904 B2 | 4/2013 | Wenchell et al. | |
| 8,423,186 B2 | 4/2013 | Itkowitz et al. | |
| 8,435,171 B2 | 5/2013 | Sholev | |
| 8,496,152 B2 | 7/2013 | Viola | |
| 8,518,024 B2 | 8/2013 | Williams et al. | |
| 8,523,900 B2 | 9/2013 | Jinno et al. | |
| 8,540,748 B2 | 9/2013 | Murphy et al. | |
| 8,562,592 B2 | 10/2013 | Conlon et al. | |
| 8,568,444 B2 | 10/2013 | Cunningham | |
| 8,579,176 B2 | 11/2013 | Smith et al. | |
| 8,591,397 B2 | 11/2013 | Berkelman et al. | |
| 8,602,287 B2 | 12/2013 | Yates et al. | |
| 8,603,077 B2 | 12/2013 | Cooper et al. | |
| 8,617,203 B2 | 12/2013 | Stefanchik et al. | |

(56) References Cited

U.S. PATENT DOCUMENTS

| | | |
|---|---|---|
| 8,663,270 B2 | 3/2014 | Donnigan et al. |
| 8,668,689 B2 | 3/2014 | Dumbauld et al. |
| 8,668,702 B2 | 3/2014 | Awtar et al. |
| 8,690,755 B2 | 4/2014 | Sholev |
| 8,696,666 B2 | 4/2014 | Sanai et al. |
| 8,709,000 B2 | 4/2014 | Madhani et al. |
| 8,761,930 B2 | 6/2014 | Nixon |
| 8,768,509 B2 | 7/2014 | Unsworth |
| 8,792,688 B2 | 7/2014 | Unsworth |
| 8,801,752 B2 | 8/2014 | Fortier et al. |
| 8,816,628 B2 | 8/2014 | Nowlin et al. |
| 8,818,560 B2 | 8/2014 | Kishi |
| 8,821,480 B2 | 9/2014 | Burbank |
| 8,827,135 B2 | 9/2014 | Amid et al. |
| 8,828,046 B2 | 9/2014 | Stefanchik et al. |
| 8,845,517 B2 | 9/2014 | Russo |
| 8,845,622 B2 | 9/2014 | Paik et al. |
| 8,870,049 B2 | 10/2014 | Amid et al. |
| 8,870,867 B2 | 10/2014 | Walberg et al. |
| 8,887,979 B2 | 11/2014 | Mastri et al. |
| 8,894,674 B2 | 11/2014 | Balanev et al. |
| 8,919,348 B2 | 12/2014 | Williams et al. |
| 8,930,027 B2 | 1/2015 | Schaible et al. |
| 8,945,098 B2 | 2/2015 | Seibold et al. |
| 8,961,499 B2 | 2/2015 | Paik et al. |
| 8,961,514 B2 | 2/2015 | Garrison |
| 8,968,187 B2 | 3/2015 | Kleyman et al. |
| 8,989,844 B2 | 3/2015 | Cinquin et al. |
| 8,992,564 B2 | 3/2015 | Jaspers |
| 9,023,015 B2 | 5/2015 | Penna |
| 9,033,998 B1 | 5/2015 | Schaible et al. |
| 9,044,238 B2 | 6/2015 | Orszulak |
| 9,084,606 B2 | 7/2015 | Greep |
| 9,113,861 B2 | 8/2015 | Martin et al. |
| 9,149,339 B2 | 10/2015 | Unsworth |
| 9,204,939 B2 | 12/2015 | Frimer et al. |
| 9,216,013 B2 * | 12/2015 | Scirica ............ A61B 17/07207 |
| 9,295,379 B2 | 3/2016 | Sholev |
| 9,307,894 B2 | 4/2016 | Von Grunberg et al. |
| 9,333,040 B2 | 5/2016 | Shellenberger et al. |
| 9,345,545 B2 | 5/2016 | Shellenberger et al. |
| 9,360,934 B2 | 6/2016 | Ruiz Morales et al. |
| 9,421,003 B2 * | 8/2016 | Williams ......... A61B 17/00234 |
| 9,474,580 B2 | 10/2016 | Hannaford et al. |
| 9,480,531 B2 | 11/2016 | Von Grunberg |
| 9,492,240 B2 | 11/2016 | Itkowitz et al. |
| 9,504,456 B2 | 11/2016 | Frimer et al. |
| 9,603,672 B2 | 3/2017 | Shellenberger et al. |
| 9,669,542 B2 | 6/2017 | Karguth et al. |
| 9,696,700 B2 | 7/2017 | Beira et al. |
| 9,757,204 B2 | 9/2017 | Frimer et al. |
| 9,757,206 B2 | 9/2017 | Frimer et al. |
| 9,795,282 B2 | 10/2017 | Sholev et al. |
| 9,795,454 B2 | 10/2017 | Seeber et al. |
| 9,877,794 B2 * | 1/2018 | Csiky ................... A61B 17/062 |
| D816,243 S | 4/2018 | Barber |
| 9,937,013 B2 | 4/2018 | Frimer et al. |
| 9,943,372 B2 | 4/2018 | Sholev et al. |
| 10,028,792 B2 | 7/2018 | Frimer et al. |
| 10,039,609 B2 | 8/2018 | Frimer et al. |
| 10,052,157 B2 | 8/2018 | Frimer et al. |
| 10,064,691 B2 | 9/2018 | Beira et al. |
| 10,071,488 B2 | 9/2018 | Robinson et al. |
| 10,092,164 B2 | 10/2018 | Sholev et al. |
| 10,092,359 B2 | 10/2018 | Beira et al. |
| 10,092,365 B2 | 10/2018 | Seeber |
| 10,136,956 B2 | 11/2018 | Seeber |
| 10,201,392 B2 | 2/2019 | Frimer et al. |
| 10,265,129 B2 | 4/2019 | Beira |
| 10,325,072 B2 | 6/2019 | Beira et al. |
| 2002/0040217 A1 | 4/2002 | Jinno |
| 2002/0049367 A1 | 4/2002 | Irion et al. |
| 2002/0072736 A1 | 6/2002 | Tierney et al. |
| 2003/0155747 A1 | 8/2003 | Bridges |
| 2003/0208186 A1 | 11/2003 | Moreyra |
| 2004/0049205 A1 | 3/2004 | Lee et al. |
| 2004/0236316 A1 | 11/2004 | Danitz et al. |
| 2004/0253079 A1 | 12/2004 | Sanchez |
| 2005/0096502 A1 | 5/2005 | Khalili |
| 2005/0204851 A1 | 9/2005 | Morley et al. |
| 2005/0240078 A1 | 10/2005 | Kwon et al. |
| 2006/0043698 A1 | 3/2006 | Bridges |
| 2006/0079884 A1 * | 4/2006 | Manzo ............... A61B 18/1442 606/41 |
| 2006/0178559 A1 | 8/2006 | Kumar et al. |
| 2006/0183975 A1 | 8/2006 | Saadat et al. |
| 2006/0219065 A1 | 10/2006 | Jinno et al. |
| 2006/0235436 A1 | 10/2006 | Anderson et al. |
| 2006/0253109 A1 | 11/2006 | Chu |
| 2007/0088340 A1 | 4/2007 | Brock et al. |
| 2007/0137371 A1 | 6/2007 | Devengenzo et al. |
| 2007/0156123 A1 | 7/2007 | Moll et al. |
| 2007/0208375 A1 | 9/2007 | Nishizawa et al. |
| 2007/0299387 A1 | 12/2007 | Williams et al. |
| 2008/0039255 A1 * | 2/2008 | Jinno ................... A61B 17/062 474/148 |
| 2008/0046122 A1 | 2/2008 | Manzo et al. |
| 2008/0058776 A1 | 3/2008 | Jo et al. |
| 2008/0071208 A1 | 3/2008 | Voegele et al. |
| 2008/0103492 A1 | 5/2008 | Morley et al. |
| 2008/0177285 A1 | 7/2008 | Brock et al. |
| 2008/0243106 A1 | 10/2008 | Coe et al. |
| 2008/0287926 A1 * | 11/2008 | Abou El Kheir .. A61B 17/3421 606/1 |
| 2008/0314181 A1 | 12/2008 | Schena |
| 2009/0030449 A1 * | 1/2009 | Kawai ................... A61B 34/30 606/205 |
| 2009/0036902 A1 | 2/2009 | Dimaio et al. |
| 2009/0198253 A1 | 8/2009 | Omori |
| 2009/0216248 A1 * | 8/2009 | Uenohara ............... A61B 17/29 606/130 |
| 2009/0216249 A1 | 8/2009 | Jinno et al. |
| 2009/0247821 A1 | 10/2009 | Rogers |
| 2009/0248039 A1 | 10/2009 | Cooper et al. |
| 2009/0275994 A1 * | 11/2009 | Phan ................... A61B 17/7064 606/86 A |
| 2009/0299141 A1 | 12/2009 | Downey et al. |
| 2010/0004508 A1 | 1/2010 | Naito et al. |
| 2010/0023025 A1 | 1/2010 | Zeiner et al. |
| 2010/0094130 A1 | 4/2010 | Ninomiya et al. |
| 2010/0121347 A1 | 5/2010 | Jaspers |
| 2010/0160929 A1 | 6/2010 | Rogers et al. |
| 2010/0160940 A1 | 6/2010 | Lutze et al. |
| 2010/0170519 A1 | 7/2010 | Romo et al. |
| 2010/0225209 A1 | 9/2010 | Goldberg et al. |
| 2010/0305595 A1 | 12/2010 | Hermann |
| 2010/0318099 A1 | 12/2010 | Itkowitz et al. |
| 2010/0318101 A1 | 12/2010 | Choi |
| 2010/0331859 A1 | 12/2010 | Omori |
| 2011/0087236 A1 | 4/2011 | Stokes et al. |
| 2011/0087238 A1 | 4/2011 | Wang et al. |
| 2011/0213346 A1 | 9/2011 | Morley et al. |
| 2011/0230867 A1 | 9/2011 | Hirschfeld et al. |
| 2011/0275901 A1 | 11/2011 | Shelton, IV |
| 2011/0276084 A1 | 11/2011 | Shelton, IV |
| 2011/0290854 A1 | 12/2011 | Timm et al. |
| 2011/0301419 A1 | 12/2011 | Craft et al. |
| 2012/0010628 A1 * | 1/2012 | Cooper ................... A61B 34/30 606/130 |
| 2012/0027762 A1 | 2/2012 | Schofield |
| 2012/0031114 A1 | 2/2012 | Mueller et al. |
| 2012/0049623 A1 | 3/2012 | Nakayama |
| 2012/0095298 A1 | 4/2012 | Stefanchik et al. |
| 2012/0116163 A1 | 5/2012 | Lutze et al. |
| 2012/0132018 A1 | 5/2012 | Tang et al. |
| 2012/0143173 A1 | 6/2012 | Steege et al. |
| 2012/0158014 A1 | 6/2012 | Stefanchik et al. |
| 2012/0191245 A1 | 7/2012 | Fudaba et al. |
| 2012/0209292 A1 | 8/2012 | Devengenzo et al. |
| 2012/0232339 A1 * | 9/2012 | Csiky ................... A61B 17/072 600/104 |
| 2012/0253326 A1 | 10/2012 | Kleyman |
| 2012/0277762 A1 | 11/2012 | Lathrop et al. |

(56) References Cited

U.S. PATENT DOCUMENTS

| | | |
|---|---|---|
| 2012/0283745 A1 | 11/2012 | Goldberg et al. |
| 2012/0289973 A1 | 11/2012 | Prisco et al. |
| 2012/0289974 A1 | 11/2012 | Rogers et al. |
| 2012/0296341 A1 | 11/2012 | Seibold et al. |
| 2013/0123805 A1* | 5/2013 | Park ............... A61B 34/30 606/130 |
| 2013/0144274 A1 | 6/2013 | Stefanchik et al. |
| 2013/0172713 A1 | 7/2013 | Kirschenman |
| 2013/0245643 A1 | 9/2013 | Woodard et al. |
| 2013/0245647 A1 | 9/2013 | Martin et al. |
| 2013/0282027 A1 | 10/2013 | Woodard et al. |
| 2013/0303408 A1 | 11/2013 | Indermuhle |
| 2013/0304083 A1 | 11/2013 | Kaercher et al. |
| 2014/0005681 A1 | 1/2014 | Gee et al. |
| 2014/0018447 A1 | 1/2014 | McGovern et al. |
| 2014/0018780 A1 | 1/2014 | Hirscheld |
| 2014/0076088 A1 | 3/2014 | Berkelman et al. |
| 2014/0114481 A1 | 4/2014 | Ogawa et al. |
| 2014/0142595 A1 | 5/2014 | Awtar et al. |
| 2014/0166023 A1 | 6/2014 | Kishi |
| 2014/0180308 A1 | 6/2014 | Von Grunberg |
| 2014/0188091 A1 | 7/2014 | Vidal et al. |
| 2014/0188159 A1 | 7/2014 | Steege |
| 2014/0200561 A1 | 7/2014 | Ingmanson et al. |
| 2014/0207150 A1 | 7/2014 | Rosa et al. |
| 2014/0230595 A1 | 8/2014 | Butt et al. |
| 2014/0249546 A1 | 9/2014 | Shvartsberg et al. |
| 2014/0263541 A1 | 9/2014 | Leimbach et al. |
| 2014/0263553 A1 | 9/2014 | Leimbach et al. |
| 2014/0276950 A1 | 9/2014 | Smaby et al. |
| 2014/0276951 A1 | 9/2014 | Hourtash et al. |
| 2014/0276956 A1 | 9/2014 | Crainich et al. |
| 2014/0350570 A1 | 11/2014 | Lee |
| 2015/0057499 A1 | 2/2015 | Erden et al. |
| 2015/0057702 A1 | 2/2015 | Edmondson et al. |
| 2015/0060517 A1 | 3/2015 | Williams |
| 2015/0066018 A1 | 3/2015 | Doll et al. |
| 2015/0105821 A1 | 4/2015 | Ward et al. |
| 2015/0142018 A1 | 5/2015 | Sniffin et al. |
| 2015/0150575 A1 | 6/2015 | Hartoumbekis et al. |
| 2015/0230869 A1 | 8/2015 | Shim et al. |
| 2015/0250547 A1 | 9/2015 | Fukushima et al. |
| 2015/0265355 A1 | 9/2015 | Prestel et al. |
| 2016/0022365 A1 | 1/2016 | Jensen et al. |
| 2016/0051274 A1 | 2/2016 | Howell et al. |
| 2016/0151115 A1 | 6/2016 | Karguth et al. |
| 2016/0374766 A1 | 12/2016 | Schuh |
| 2017/0245954 A1 | 8/2017 | Beira |
| 2017/0273749 A1 | 9/2017 | Grover et al. |
| 2017/0308667 A1 | 10/2017 | Beira et al. |
| 2017/0360522 A1 | 12/2017 | Beira |
| 2017/0367778 A1 | 12/2017 | Beira |
| 2018/0000472 A1 | 1/2018 | Beira |
| 2018/0000544 A1 | 1/2018 | Beira |
| 2018/0000550 A1 | 1/2018 | Beira |
| 2018/0028269 A1 | 2/2018 | Morel et al. |
| 2018/0055583 A1 | 3/2018 | Schuh et al. |
| 2018/0125519 A1 | 5/2018 | Beira et al. |
| 2018/0125592 A1 | 5/2018 | Beira |
| 2018/0242991 A1 | 8/2018 | Beira |
| 2018/0353252 A1 | 12/2018 | Chassot et al. |
| 2018/0360548 A1 | 12/2018 | Marshall et al. |

FOREIGN PATENT DOCUMENTS

| | | |
|---|---|---|
| CN | 101732093 A | 6/2010 |
| CN | 103717355 A | 4/2014 |
| DE | 43 03 311 A1 | 8/1994 |
| DE | 19652792 C2 | 5/1999 |
| DE | 10314827 B3 | 4/2004 |
| DE | 10314828 B3 | 7/2004 |
| DE | 10 2012 222 755 | 6/2014 |
| DE | 10 2014 205 036 A1 | 9/2015 |
| DE | 10 2014 205 159 A1 | 9/2015 |
| EP | 0 595 291 A1 | 5/1994 |
| EP | 0 621 009 A1 | 10/1994 |
| EP | 0 677 275 A2 | 10/1995 |
| EP | 1 254 642 A1 | 11/2002 |
| EP | 1 279 371 B1 | 12/2004 |
| EP | 1 886 630 A2 | 2/2008 |
| EP | 1 889 579 A2 | 2/2008 |
| EP | 2 058 090 A2 | 5/2009 |
| EP | 1 977 677 B1 | 8/2009 |
| EP | 2 095 778 A1 | 9/2009 |
| EP | 1 889 583 B1 | 4/2011 |
| EP | 2 377 477 B1 | 5/2012 |
| EP | 2 473 119 A2 | 7/2012 |
| EP | 2 305 144 B1 | 10/2012 |
| EP | 2 044 893 B1 | 7/2013 |
| EP | 2 653 110 A1 | 10/2013 |
| EP | 2 679 192 A2 | 1/2014 |
| EP | 2 736 680 A2 | 6/2014 |
| EP | 2 777 561 A1 | 9/2014 |
| EP | 2 783 643 A1 | 10/2014 |
| EP | 2 837 340 A1 | 2/2015 |
| EP | 2 837 354 A1 | 2/2015 |
| EP | 2 554 131 B1 | 8/2015 |
| EP | 2 979 657 A1 | 2/2016 |
| GB | 0 834 244 | 5/1960 |
| GB | 0 969 899 A | 9/1964 |
| JP | 2004-041580 A | 2/2004 |
| JP | 2007-290096 A | 11/2007 |
| JP | 2008-104620 A | 5/2008 |
| JP | 2009-018027 A | 1/2009 |
| KR | 20110032444 A | 3/2011 |
| KR | 20130031403 A | 3/2013 |
| WO | WO-82/00611 A1 | 3/1982 |
| WO | WO-03/067341 A2 | 8/2003 |
| WO | WO-03/086219 A2 | 10/2003 |
| WO | WO-2004/052171 A2 | 6/2004 |
| WO | WO-2005/009482 A2 | 2/2005 |
| WO | WO-2005/046500 A1 | 5/2005 |
| WO | WO-2006/086663 A2 | 4/2006 |
| WO | WO-2007/133065 A1 | 11/2007 |
| WO | WO-2008/130235 A2 | 10/2008 |
| WO | WO-2009/091497 A2 | 7/2009 |
| WO | WO-2009/095893 A2 | 8/2009 |
| WO | WO-2009/145572 A1 | 12/2009 |
| WO | WO-2009/157719 A2 | 12/2009 |
| WO | WO-2010/019001 A2 | 2/2010 |
| WO | WO-2010/030114 A2 | 3/2010 |
| WO | WO-2010/050771 A2 | 5/2010 |
| WO | WO-2010/083480 A2 | 7/2010 |
| WO | WO-2010/096580 A1 | 8/2010 |
| WO | WO-2010/130817 A1 | 11/2010 |
| WO | WO-2011/025818 A1 | 3/2011 |
| WO | WO-2011/027183 A1 | 3/2011 |
| WO | WO-2011/123669 A1 | 10/2011 |
| WO | WO-2012/020386 A1 | 2/2012 |
| WO | WO-2012/049623 A1 | 4/2012 |
| WO | WO-2013/014621 A1 | 1/2013 |
| WO | WO-2014/012780 A1 | 1/2014 |
| WO | WO-2014/018447 A1 | 1/2014 |
| WO | WO-2014/067804 A1 | 5/2014 |
| WO | WO-2014/094716 A1 | 6/2014 |
| WO | WO-2014/094717 | 6/2014 |
| WO | WO-2014/094718 | 6/2014 |
| WO | WO-2014/094719 | 6/2014 |
| WO | WO-2014/145148 A2 | 9/2014 |
| WO | WO-2014/156221 A1 | 10/2014 |
| WO | WO-2014/201010 A1 | 12/2014 |
| WO | WO-2014/201538 A1 | 12/2014 |
| WO | WO-2015/081946 A1 | 6/2015 |
| WO | WO-2015/081947 A1 | 6/2015 |
| WO | WO-2015/088647 A1 | 6/2015 |
| WO | WO-2015/088655 A1 | 6/2015 |
| WO | WO-2015/111475 A1 | 7/2015 |
| WO | WO-2015/113933 A1 | 8/2015 |
| WO | WO-2015/129383 A1 | 8/2015 |
| WO | WO-2015/139674 A1 | 9/2015 |
| WO | WO-2015/175200 A1 | 11/2015 |
| WO | WO-2016/083189 A1 | 6/2016 |
| WO | WO-2016/154173 A1 | 9/2016 |

(56) References Cited

FOREIGN PATENT DOCUMENTS

| WO | WO-2016/183054 A1 | 11/2016 |
|---|---|---|
| WO | WO-01/6189284 A1 | 12/2016 |
| WO | WO-2016/189284 A1 | 12/2016 |
| WO | WO-2017/015599 A1 | 1/2017 |
| WO | WO-2017/064301 A1 | 4/2017 |
| WO | WO-2017/064303 A1 | 4/2017 |
| WO | WO-2017/064305 A1 | 4/2017 |
| WO | WO-2017/064306 A1 | 4/2017 |
| WO | WO-2017/220978 A1 | 12/2017 |
| WO | WO-2018/142112 A1 | 8/2018 |
| WO | WO-2018/162921 A1 | 9/2018 |

OTHER PUBLICATIONS

Abbott, et al., "Design of an Endoluminal NOTES Robotic System," IEEE/RSJ International Conference on Intelligent Robots and Systems, San Diego, CA, pp. 410-416 (2007).
Aesculap Surgical Technologies, Aesculap® Caiman® , Advanced Bipolar Seal and Cut Technology Brochure, 6 pages (retrieved Aug. 31, 2015).
Arata, et al., "Development of a dexterous minimally-invasive surgical system with augmented force feedback capability," IEEE/RSJ International Conference on Intelligent Robots and Systems, pp. 3207-3212 (2005).
Çavuşoğlu, et al., "Laparoscopic Telesurgical Workstation," IEEE Transactions on Robotics and Automation,(15)4:728-739 (1999).
Dachs, et al., "Novel Surgical Robot Design: Minimizing the Operating Envelope Within the Sterile Field," 28th International Conference, IEEE Engineering in Medicine Biology Society, New York, pp. 1505-1508 (2006).
Dario, et al., "Novel Mechatronic Tool for Computer-Assisted Arthroscopy," IEEE Transactions on Information Technology in Biomedicine, 4(1):15-29 (Mar. 2000).
Focacci, et al., "Lightweight Hand-held Robot for Laparoscopic Surgery," IEEE International Conference on Robotics & Automation, Rome, Italy, pp. 599-604 (2007).
Guthart, et al., "The Intuitive™ Telesurgery System: Overview and Application," IEEE International Conference on Robotics & Automation, San Francisco, CA, pp. 618-621 (2000).
Ikuta, et al., "Development of Remote Microsurgery Robot and New Surgical Procedure for Deep and Narrow Space," IEEE International Conference on Robotics & Automation, Taipei, Taiwan, pp. 1103-1108 (2003).
Ikuta, et al., "Hyper Redundant Miniature Manipulator 'Hyper Finger' for Remote Minimally Invasive Surgery in Deep Area," IEEE International Conference on Robotics & Automation, Taipei, Taiwan, pp. 1098-1102 (2003).
International Search Report & Written Opinion dated Feb. 2, 2017 in Int'l PCT Patent Appl. Serial No. PCT/IB2016/001286.
International Search Report & Written Opinion dated Jan. 18, 2013 in Int'l PCT Patent Appl Serial No. PCT/IB2012/053786.
International Search Report dated Jan. 18, 2013 in Int'l PCT Patent Appl Serial No. PCT/IB2012/053786.
International Search Report dated Mar. 23, 2012 in Int'l PCT Patent Appl Serial No. PCT/IB2011/054476.
Ishii, et al., "Development of a New Bending Mechanism and Its Application to Robotic Forceps Manipulator," IEEE International Conference on Robotics & Automation, Rome, Italy, pp. 238-243 (2007).
International Search Report & Written Opinion dated May 23, 2016 in Int'l PCT Patent Appl Serial No. PCT/IB2015/002524.
International Search Report & Written Opinion dated Mar. 30, 2015 in Int'l PCT Patent Appl Serial No. PCT/EP2015/051473.
International Search Report & Written Opinion dated Apr. 26, 2016 in Int'l PCT Patent Appl Serial No. PCT/IB2015/002512.

International Search Report & Written Opinion dated May 24, 2016 in Int'l PCT Patent Appl Serial No. PCT/IB2015/002487.
International Search Report & Written Opinion dated Jun. 10, 2016 in Int'l PCT Patent Appl Serial No. PCT/IB2015/002533.
International Search Report & Written Opinion dated Jun. 13, 2016 in Int'l PCT Patent Appl Serial No. PCT/IB2015/002493.
International Search Report & Written Opinion dated Aug. 25, 2016 in Int'l PCT Patent Appl Serial No. PCT/IB2016/000542.
International Search Report & Written Opinion dated Sep. 2, 2016 in Int'l PCT Patent Appl Serial No. PCT/IB2016/000543.
Kobayashi, et al., "Small Occupancy Robotic Mechanisms for Endoscopic Surgery," International Conference on Medical Image Computing and Computer assisted Interventions, pp. 75-82 (2002).
Mayer, et al., "The Endo[PA]R System for Minimally Invasive Robotic Surgery," IEEE/RSJ International Conference on Intelligent Robots and Systems, Sendai, Japan, pp. 3637-3642 (2004).
Mitsuishi, et al., "Development of a Remote Minimally Invasive Surgical System with Operational Environment Transmission Capability," IEEE International Conference on Robotics & Automation, Taipei, Taiwan, pp. 2663-2670 (2003).
Nakamura, et al., "Multi-DOF Forceps Manipulator System for Laparoscopic Surgery-Mechanism miniaturized & Evaluation of New Interface," 4th International Conference on Medical Image Computing and Computer assisted Interventions (MICCAI2001), pp. 606-613 (2001).
Peirs, et al., "Design of an advanced tool guiding system for robotic surgery," IEEE International Conference on Robotics & Automation, Taipei, Taiwan, pp. 2651-2656 (2003).
Sallé, et al., "Optimal Design of High Dexterity Modular MIS Instrument for Coronary Artery Bypass Grafting," IEEE International Conference on Robotics & Automation, New Orleans, LA, pp. 1276-1281 (2004).
Seibold, et al., "Prototype of Instrument for Minimally Invasive Surgery with 6-Axis Force Sensing Capability," IEEE International Conference on Robotics & Automation, Barcelona, Spain, pp. 496-501 (2005).
Simaan et al., "Dexterous System for Laryngeal Surgery: Multi-Backbone Bending Snake-like Slaves for Teleoperated Dexterous Surgical Tool Manipulation," IEEE International Conference on Robotics & Automation, New Orleans, LA, pp. 351-357 (2004).
Stryker® , Endoscopy, Take a Look Around, Ideal Eyes™ FFD122 HD, Articulating Laparoscope Brochure, 2 pages. (2009).
Swiss Search Report dated Jun. 4, 2012 in Swiss Patent Application No. CH 00702/12.
Tavakoli, et al., "Force Reflective Master-Slave System for Minimally Invasive Surgery," IEEE/RSJ International Conference on Intelligent Robots and Systems, Las Vegas, NV, pp. 3077-3082 (2003).
Taylor, et al., "Steady-Hand Robotic System for Microsurgical Augmentation," The International Journal of Robotics Research, 18(12):1201-1210 (1999).
www.cttc.co/technologies/maestro-non-robotic-dexterous-laproscopic-instrument-writs-providing-seven-degrees, "Maestro: Non-Robotic Dexterous Laproscopic Instrument With a Wrist Providing Seven Degrees of Freedom", accessed Nov. 12, 2015, 4 pages.
Yamashita, et al., "Development of Endoscopic Forceps Manipulator Using Multi-Slider Linkage Mechanisms," The 1st Asian Symposium on Computer Aided Surgery-Robotic and Image-Guided Surgery, Ibaraki, Japan, 4 pages (2005).
Zeus, "Robotic Surgical System" available at http://al-laboutroboticsurgery.com/zeusrobot.html.
Communication Relating to the Results of the Partial International Search dated May 28, 2019 in Int'l PCT Patent Appl. Serial No. PCT/IB2019/050961.
International Search Report & Written Opinion dated Jul. 10, 2018 in Int'l PCT Patent Appl. Serial No. PCT/IB2018/053272.

* cited by examiner

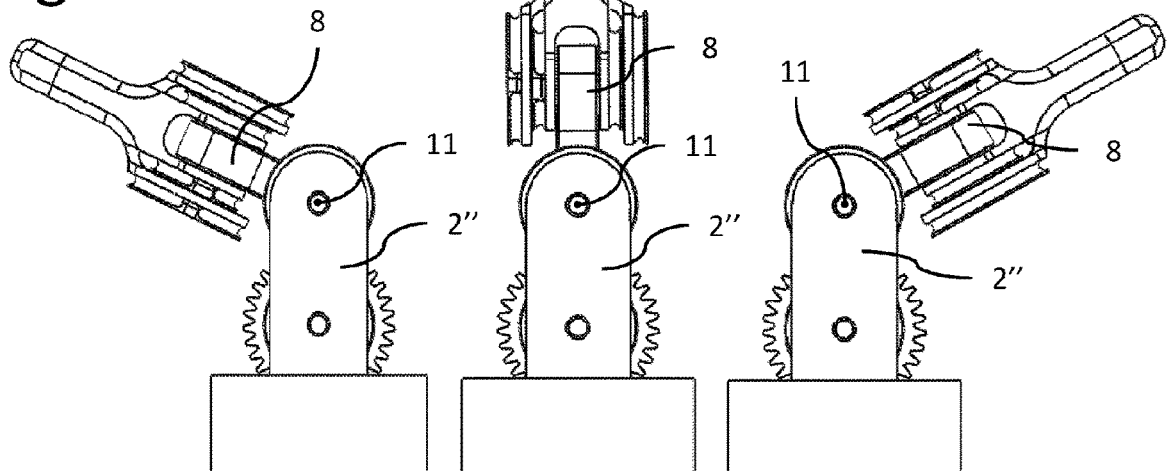

REUSABLE SURGICAL INSTRUMENT FOR MINIMALLY INVASIVE PROCEDURES

FIELD OF THE INVENTION

The present invention relates to the field of minimally invasive articulated instruments such as graspers, dissectors, and scissors, wherein the orientation of the distal end effector in relation to the instrument shaft is able to be controlled. More particularly, the invention relates to reusable surgical instruments that have to be cleaned and sterilized after each procedure. Most specifically, the invention relates to such instruments wherein the actuation and orientation of the distal end-effector is remotely performed, from the proximal to the distal extremity of the instrument shaft, by mechanical transmission elements. The instrument of the present invention is intended to be used primarily in surgical procedures, wherein instruments with articulated end-effectors are passed through incisions or trocars into a patient's body cavity, which may be optionally inflated with insufflation gas.

BACKGROUND OF THE INVENTION

Open surgery is still the standard technique for most surgical procedures. It has been used by the medical community for several decades and consists of performing the surgical tasks by a long incision in the abdomen or other body cavity, through which traditional surgical tools are inserted. However, due to the long incision, this approach is extremely invasive for the patient, resulting in substantial blood loss during the surgery and long and painful recovery periods in an in-patient setting.

In order to reduce the invasiveness of open surgery, laparoscopy, a minimally invasive technique, was developed. Instead of a single long incision, one or more smaller incisions are made in the patient through which long and thin surgical instruments and endoscopic cameras are inserted. Because of the low degree of invasiveness, laparoscopic techniques reduce blood loss and pain while also shortening hospital stays. When performed by experienced surgeons, these techniques can attain clinical outcomes similar to open surgery. However, despite the above-mentioned advantages, laparoscopy requires advanced surgical skills to manipulate the rigid and long instrumentation through small incisions in the patient.

Traditionally, laparoscopic instruments, such as graspers, dissectors, scissors and other tools, have been mounted on straight shafts. These shafts are inserted through small incisions into the patient's body and, because of that, their range of motion inside the body is reduced. The entry incision acts as a point of rotation, decreasing the freedom of the surgeon for positioning and orienting the instruments inside the patient. Therefore, due to the drawbacks of its instrumentation, laparoscopic procedures are mainly limited to use in simple surgeries, while only a small minority of surgeons is able to use them in complex procedures. Therefore, there has been a clear trend for providing distal articulations to end-effector elements of laparoscopic instruments, allowing the distal effector elements to be angulated with respect to the longitudinal axis of the instrument shaft.

Laparoscopic instruments can be provided as disposable or reusable medical devices. Disposable devices are thrown away after each utilization, without having the need to be cleaned. On the other hand, reusable devices must be cleaned and sterilized after each procedure. In many instances, cost-effectiveness and operating room efficiency requires that instruments be cleaned, sterilized and re-used.

Although techniques such as steam sterilization have been widely used, they are often insufficient to reach all of the blood and tissue residues that can enter a surgical instrument during a surgical procedure. In particular, for the case of instruments with articulated end-effectors (like the one disclosed in U.S. Pat. No. 7,819,894), the cleaning and sterilization processes are even more challenging. The higher mechanical complexity of the articulated end-effector brings additional places where tissue and blood can easily infiltrate. In addition, in order to be airtight and keep the body cavity inflated, these systems are constructed with an elongated and closed tubular body, from where the penetrated blood and tissue are very difficult to be removed.

Some reusable laparoscopic instruments (like to ones disclosed in EP1889579, U.S. Pat. Nos. 5,147,357, 5,304, 203, 5,308,358, 5,368,606, 5,603,723 and US20090299141) can be disassembled for cleaning and thereafter reassembled for subsequent utilization. This enables access to the interior portions of the instrument tube and the internal mechanical elements housed therein, which results in more reliable cleaning and sterilization methods. However, this solution has only been used in instruments with low complexity end-effectors (mainly with a single distal degree of freedom), where the assembly and disassembly procedures are relatively simple and can therefore be easily accomplished by the hospital staff. This easy assembly/disassembly procedure cannot be applied to existing articulated instruments (like the one disclosed in U.S. Pat. No. 7,819,894). Indeed, in these instruments, the external tube of the instrument's shaft has the double function of giving structure to the instrument shaft and providing a sealing function for the instrument with respect to the trocar in order to preserve the inflation of the abdominal cavity where the instrument is operated. This limitation in the design of existing articulated instruments makes it impossible to remove the outer tube, which poses a significant challenge for the cleaning and sterilization of such instruments. Without being able to remove the outer tube, direct access to the internal elements of the articulated instrument is not possible, meaning that cleaning tools cannot be directly applied to the elements requiring cleaning, despite the fact that blood and tissue may have contaminated these elements during a surgical procedure. While some articulated instruments allow for the passage of a stream of water as a method of cleaning the internal elements, this does not provide for complete cleaning and is not an efficient solution.

Accordingly, an aim of the present invention is to overcome the aforementioned drawbacks of known devices by providing a new surgical instrument with an articulated end-effector, with uses in a cable-driven surgical instrument, where the external tube composing the instrument's shaft can be easily removed, for efficient cleaning, and subsequently reassembled for utilization.

SUMMARY OF THE INVENTION

Theses aims and other advantages are achieved by a new articulated and reusable surgical instrument in the form of, for example, a dissector, scissor or grasper. The instrument comprises an articulated end-effector, placed at the distal extremity of an instrument shaft, which comprises an internal structural element and an external tube. The shaft defines the longitudinal axis of the instrument and is able to move according to the mobility constraints imposed by a body incision, which includes a rotational movement about its own axis. This rotation also causes the rotation of the end-effector, mounted on the distal extremity of the shaft. Thus, the instrument shaft has the triple function of (1) positioning the end-effector within the interior of the patient's body, (2) allowing the passage of the different transmission elements that are able to actuate the different distal end-effector articulations and (3) avoiding the passage of air through the instrument, in order to maintain the inflation of the body cavity where the instrument is operating. While the two first functions are achieved by the internal structural element, the third function is primarily achieved by the external tube. Since its primary function is not mechanical, the external tube can be easily and individually detached from the instrument after each procedure. This enables proper access to the internal elements passing through and disposed on the shaft so that the instrument can be more effectively cleaned and sterilized. Finally, the external tube can be easily re-attached to the instrument for the next usage.

With the above mentioned features, this reusable instrument can combine the performance benefits of highly articulated instruments with the benefits of most simple laparoscopic instrumentation, which can be easily and almost completely assembled and disassembled by the hospital staff so that internal components can be accessed for a more effective cleaning and sterilization. This results in a unique combination of safety and performance that is currently not available.

BRIEF DESCRIPTION OF THE FIGURES

The invention will be better understood according to the following detailed description of several embodiments with reference to the attached drawings, in which:

FIG. 5 shows an articulated end-effector according to an embodiment of the present invention in a first active position;

FIG. 6 shows an articulated end-effector according to an embodiment of the present invention in a second active position;

FIG. 7 shows an articulated end-effector according to an embodiment of the present invention in a third active position;

DETAILED DESCRIPTION OF THE INVENTION

Figure 1:
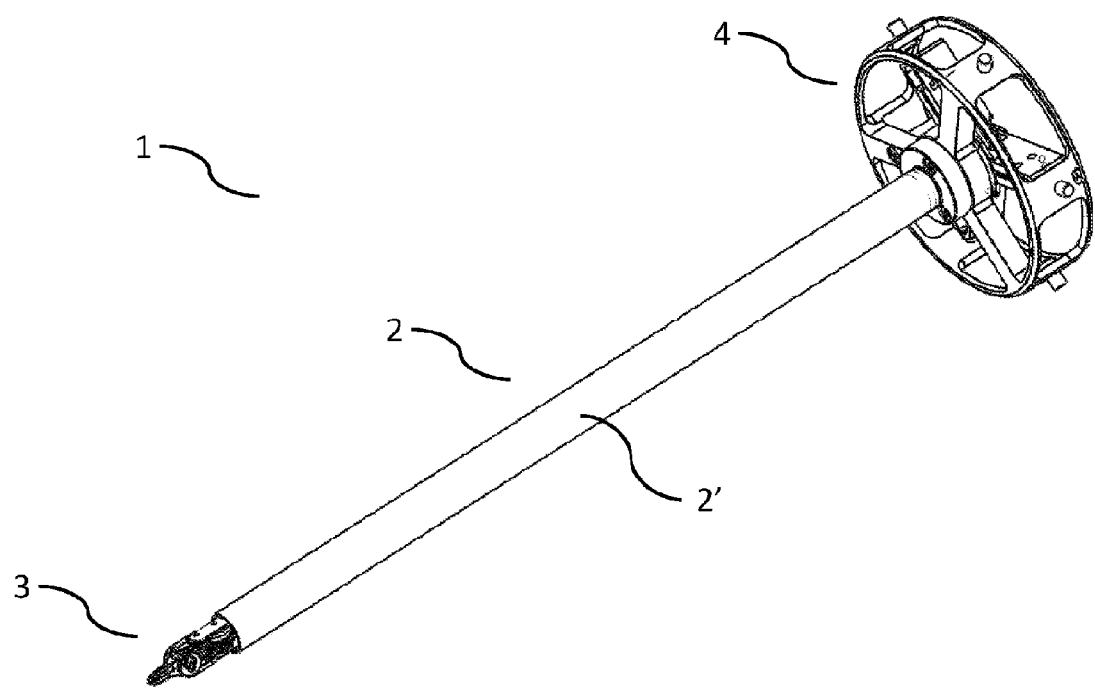
FIG. 1 shows a perspective view of a reusable surgical instrument according to an embodiment of the invention.
Figure 2:
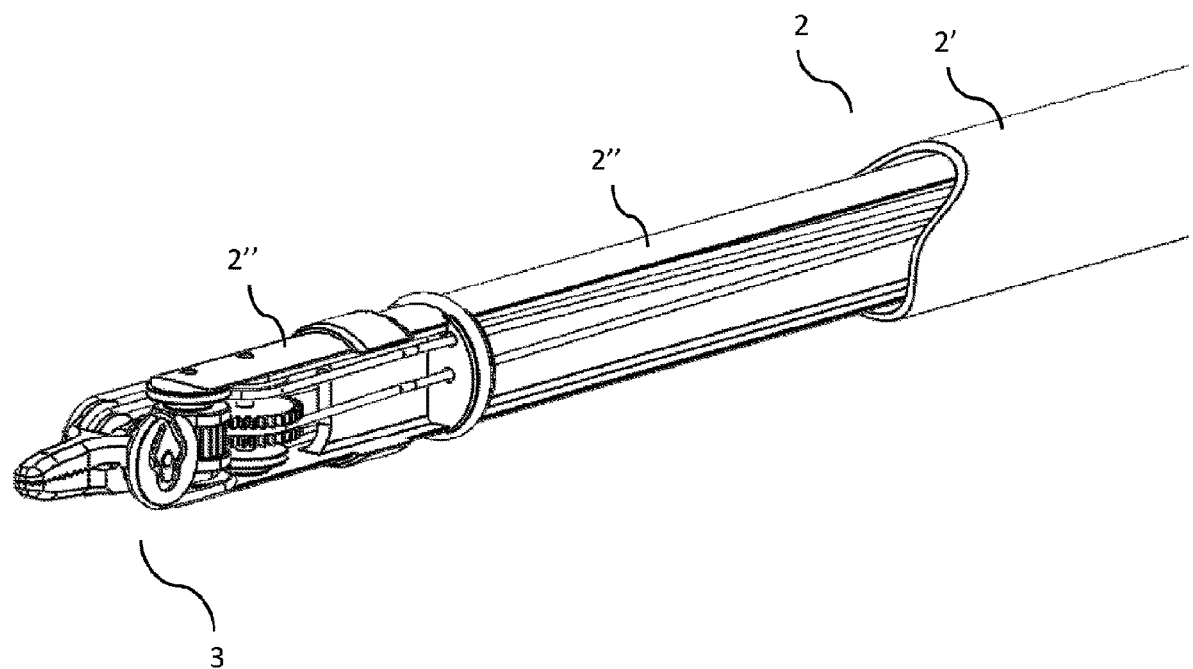
FIG. 2 shows a perspective view of a reusable surgical instrument according to an embodiment of the present invention with a schematic cutout of the external tube of the instrument shaft, through which is it possible to see the internal structural elements passing through the instrument shaft.
Figure 3:
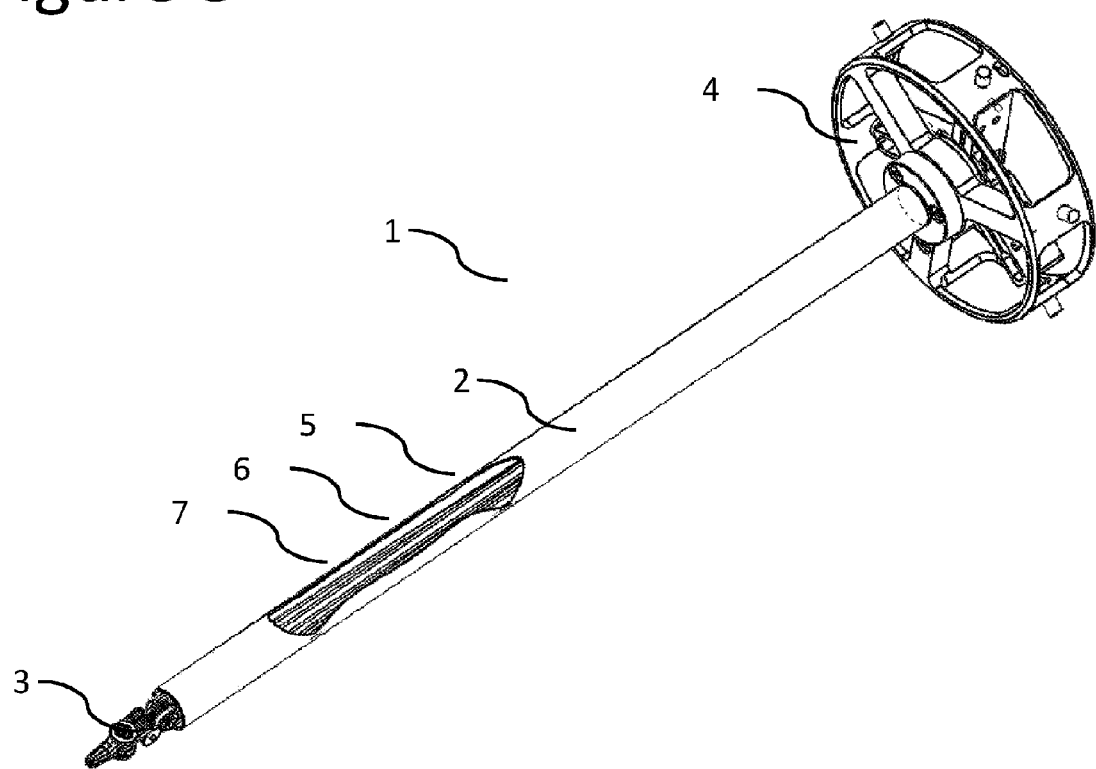
FIG. 3 shows a perspective view of a reusable surgical instrument according to an embodiment of the present invention with a schematic cutout of the external tube of the instrument shaft, through which is it possible to see different mechanical transmission elements.
Figure 4:
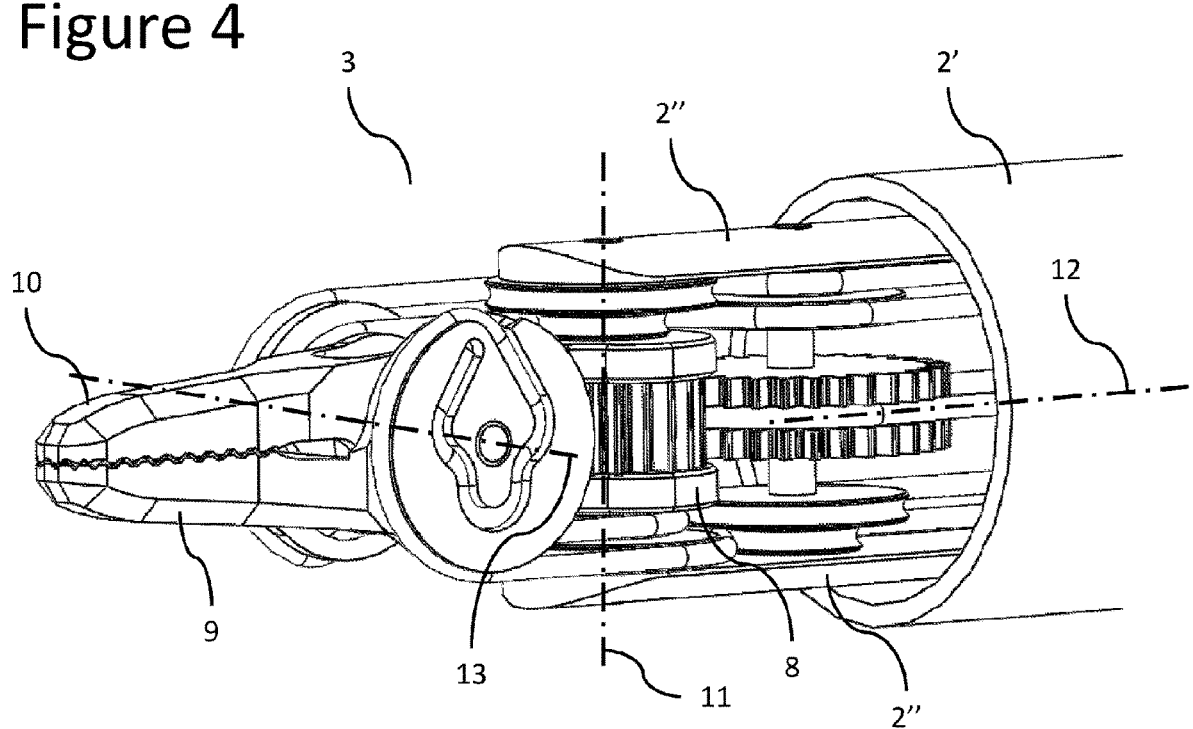
FIG. 4 shows a perspective view of an articulated end-effector of a reusable surgical instrument according to an embodiment of the invention.
Figure 8:
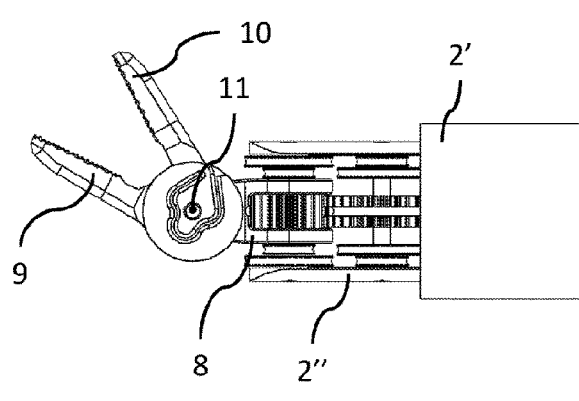
FIG. 8 shows an articulated end-effector according to an embodiment of the present invention in a fourth active position.
Figure 9:
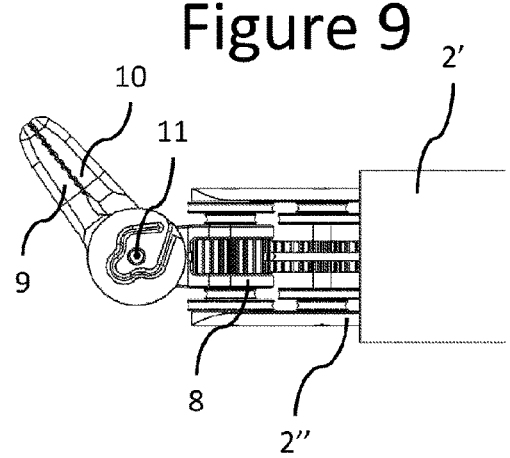
FIG. 9 shows an articulated end-effector according to an embodiment of the present invention in a fifth active position.

A reusable surgical instrument 1 for minimally invasive surgical procedures, with a detachable external tube 2', constructed in accordance with an embodiment of the present invention, is described herein, and is seen generally in FIG. 1. This instrument 1 includes a main shaft 2, a distal articulated end-effector 3 and a proximal hub 4. Referring to FIG. 2, the shaft 2 is composed of two different elements: an internal structural element 2" and an external tube 2'. The internal structural element 2" provides a stable positioning to the end-effector 3 and to allow the passage of the different mechanical elements 5, 6, 7 that are able to deliver motion to the different end-effector links 8, 9, 10 from the proximal hub 4 at the proximal extremity of the instrument (FIGS. 3 and 4). The external tube 2' protects the internal elements on the shaft 2 when passing through the incision and avoids the passage of air through the instrument 1, in order to maintain the inflation of the body cavity where the instrument 1 is operating.

Figure 10:
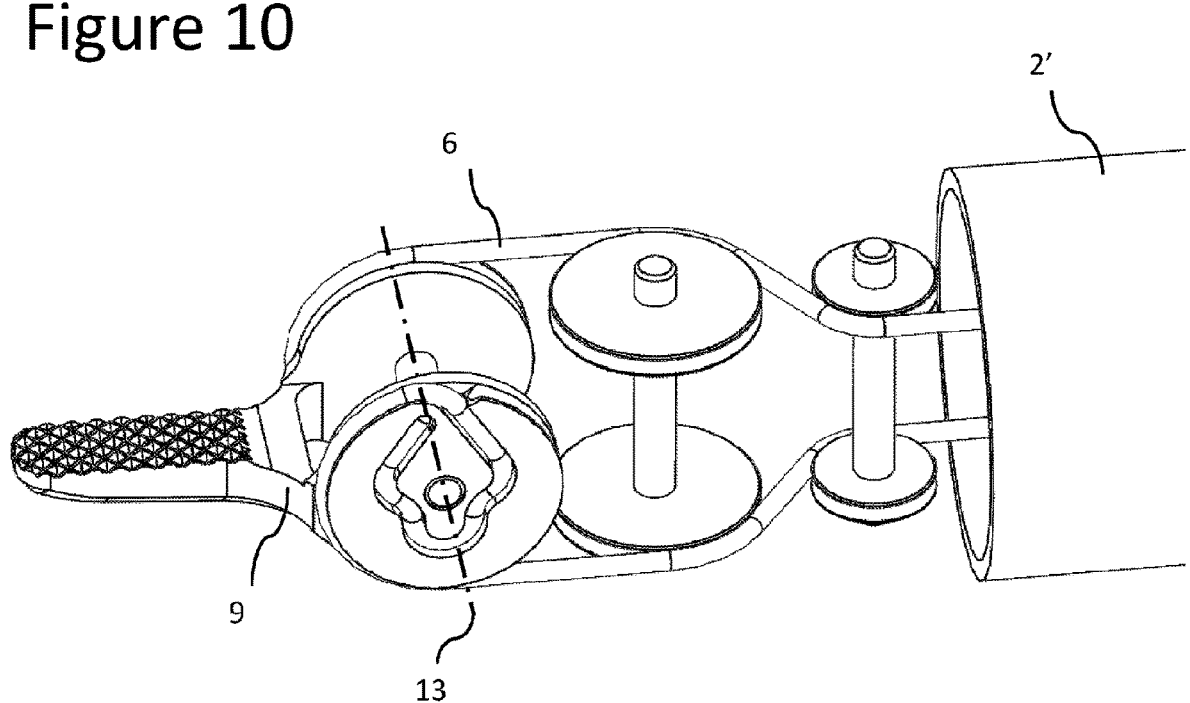
FIG. 10 shows actuation topology for a first distal end-effector link according to an embodiment of the present invention.
Figure 11:
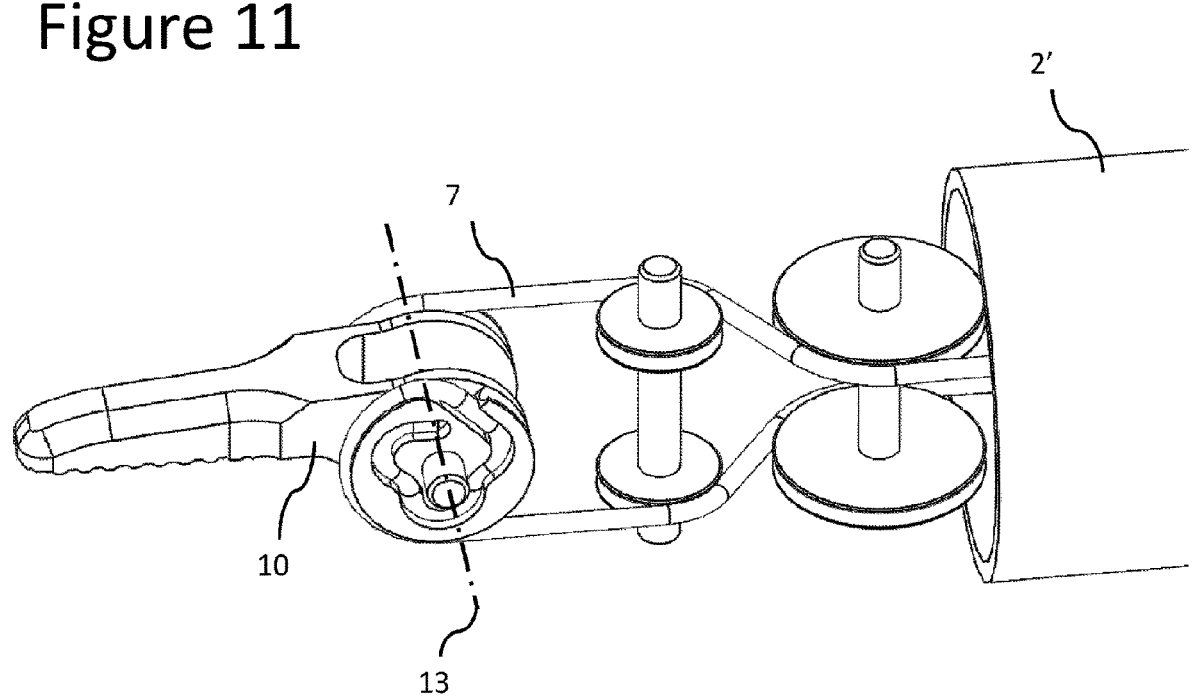
FIG. 11 shows actuation topology for a second distal end-effector link according to an embodiment of the present invention.
Figure 12:
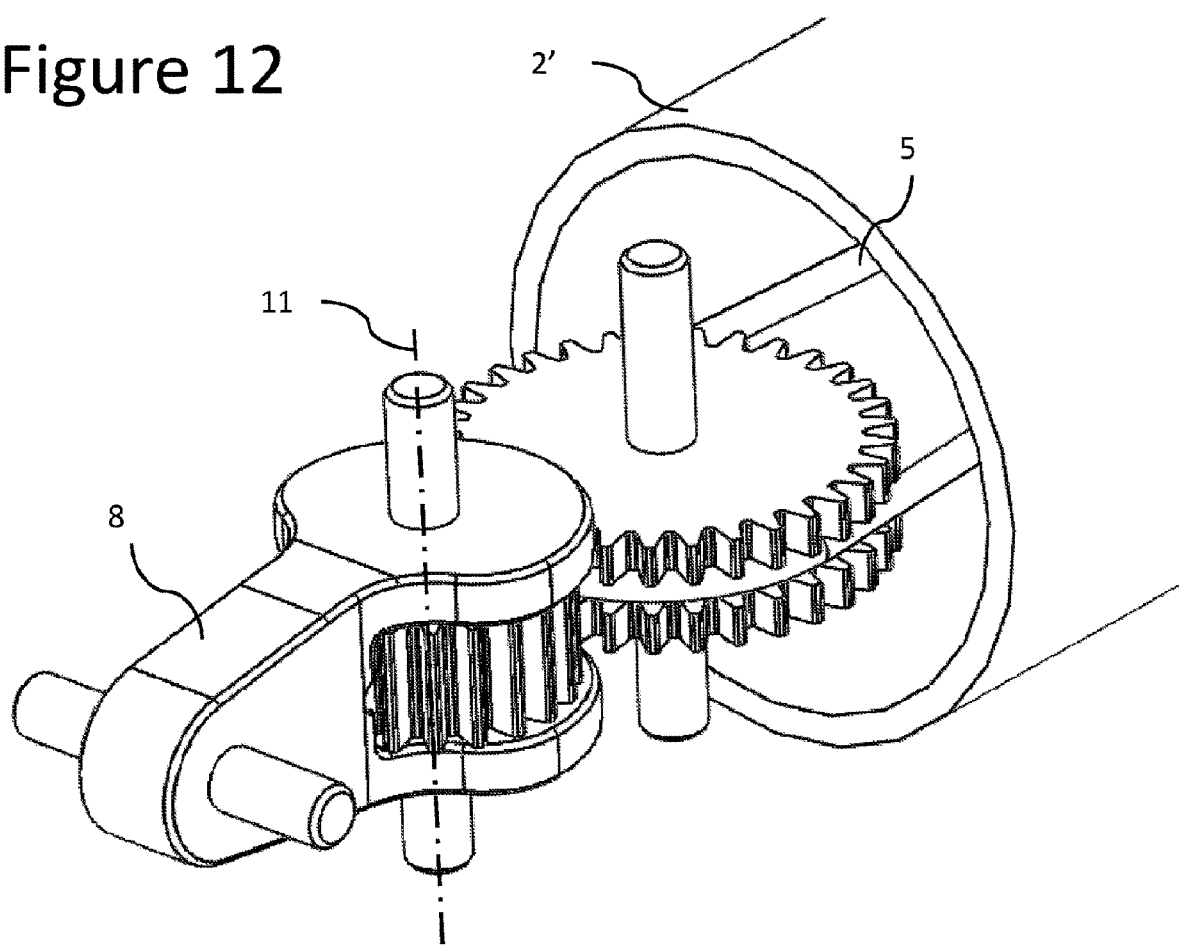
FIG. 12 shows actuation topology for a proximal end-effector link according to an embodiment of the present invention.

Referring still to FIG. 4, the end-effector 3 is connected to the internal structural element 2" by a proximal joint, which allows the rotation of the proximal end-effector link 8 about the proximal axis 11 in such a manner that the orientation of the proximal end-effector link 8 with respect to the main shaft axis 12 can be changed. The distal end-effector links 9, 10 are rotatably connected to the proximal end-effector link 8 by two distal joints, having coincident axes of rotation, which are represented by the distal axis 13. This distal axis 13 is substantially perpendicular and non-intersecting with the proximal axis 11 and substantially intersects the main shaft axis 12. FIGS. 5 to 9 show the surgical instrument 1 with different angular displacements at the end-effector joints. FIGS. 10 to 12 show the connection between the transmission element 5, 6, 7 and the end-effector links 8, 9, 10.

Figure 13:
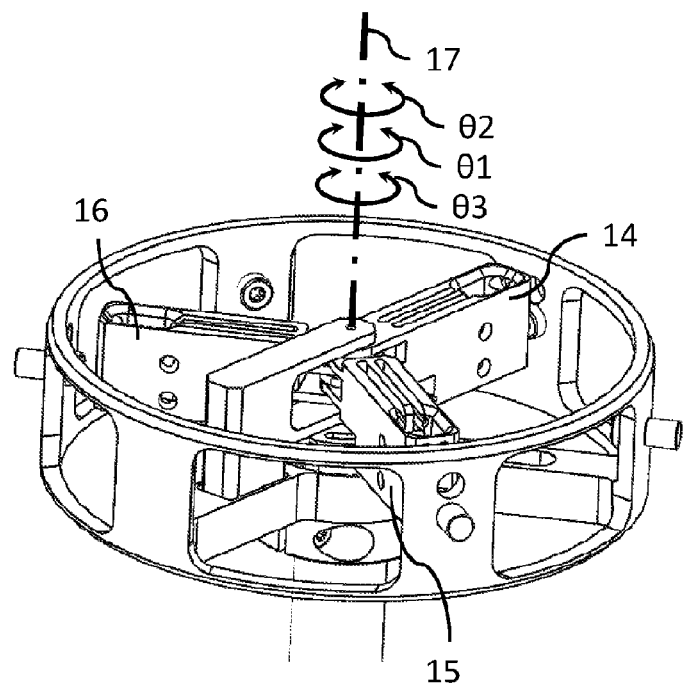
FIG. 13 shows a perspective view of proximal hub with different proximal rotating elements according to an embodiment of the present invention.
Figure 14:
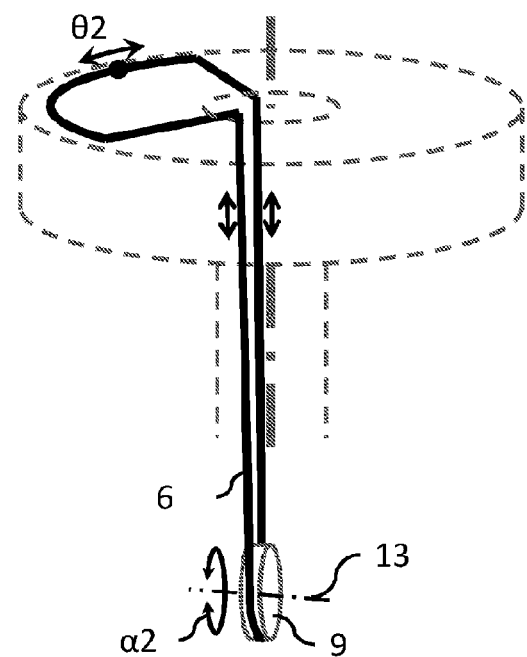
FIG. 14 shows a simplified path of a flexible transmission element actuating a distal articulation of an end-effector according to an embodiment of the present invention.

With reference to FIGS. 13 and 14, the movement is transmitted to each one of the three distal articulations of the instrument 1 by a rotating element 14, 15, 16, which is able to rotate about an axis 17 and is connected to a transmission element 5, 6, 7. As a result, when the rotating element 14, 15, 16 rotates a certain angle θ1, θ2, θ3 about the axis 17, a rotation α1, α2, α3 is transmitted to the respective end-effector member 8, 9, 10.

Figure 15:
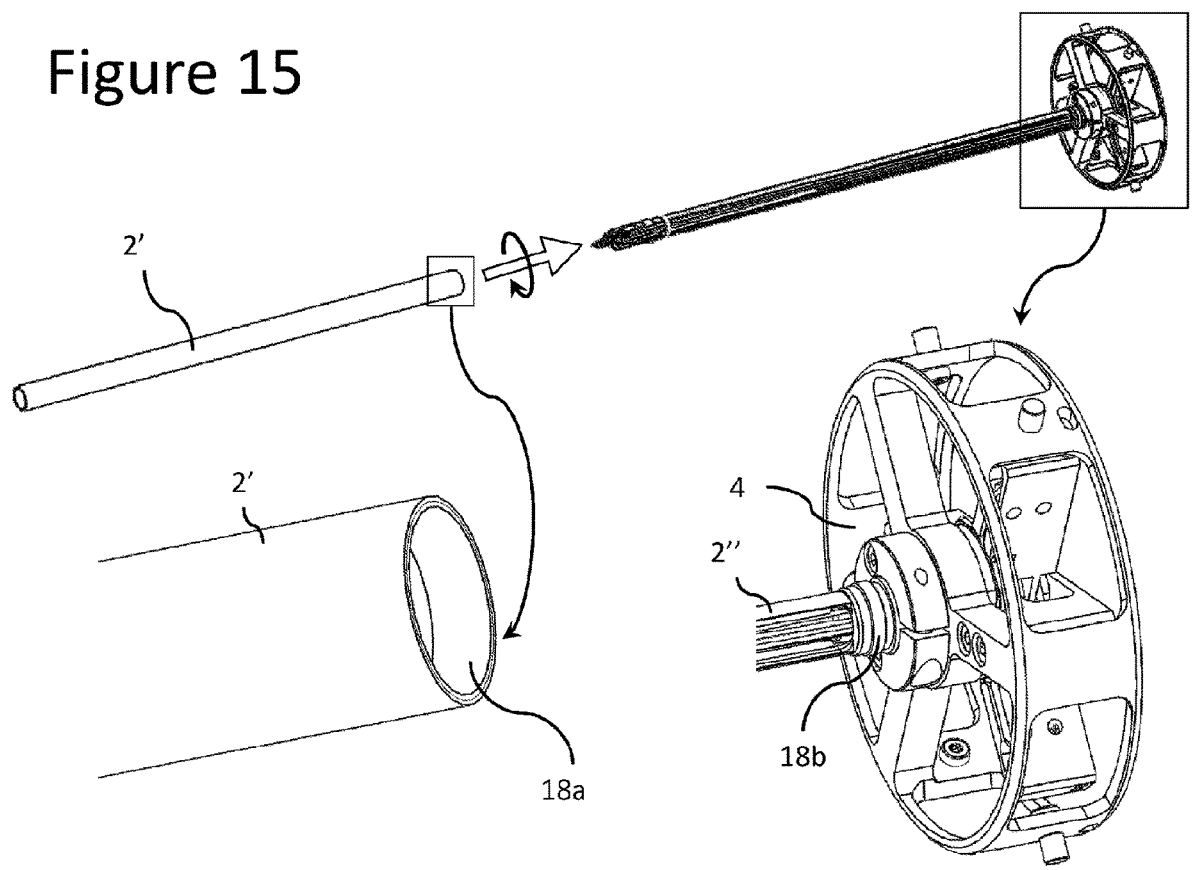
FIG. 15 shows a procedure through which an external tube of an instrument shaft can be assembled and disassembled on a reusable surgical instrument according to an embodiment of the present invention.
Figure 16:
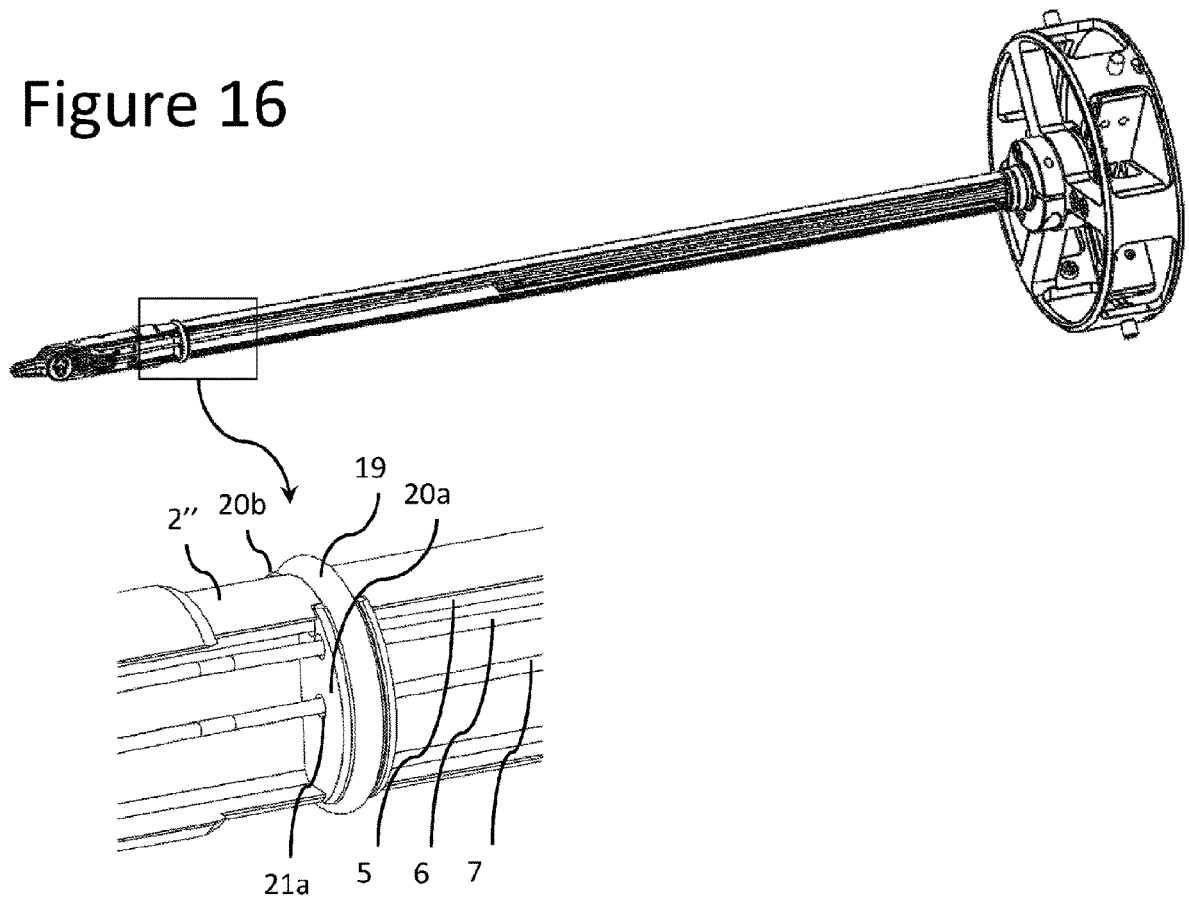
FIG. 16 shows a detailed perspective view of sealing and transversal elements mounted on an internal structural element according to an embodiment of the present invention.

The external tube 2' can be easily and individually detached and attached to the instrument 1 after each procedure. Referring to FIG. 15, the internal structural element 2" is fixed directly to the proximal hub 4 and the external tube 2' can be connected and disconnected from the internal structural element 2" at the threaded surfaces 18a and 18b. Therefore, with this architecture, the external tube 2' can be removed from the instrument 1, without the need to disassemble other parts of the system, like the articulated end-effector 3 or the mechanical transmission elements 5, 6, 7, which remain completely operational from a mechanical perspective without the external tube 2'. This feature facilitates the effective cleaning and sterilization of the instrument 1, which can easily be performed by the hospital staff.

Towards a more distal region of the instrument shaft 2, the external tube 2' is in contact with a sealing element 19, which fills the gap between the internal surface of the external tube 2' and the two transversal elements 20a, 20b that are mounted on the internal structural element 2". These two transversal elements 20a, 20b have small channels 21a, 21b, 21c, 21d, 21e, 21f through which the transmission elements 5, 6, 7 can pass, guaranteeing the air-tightness of the instrument 1.

In some embodiments of the present invention, the mechanical transmission elements 5, 6, 7 may comprise ropes, whose tension can be released after each procedure, so that the cleaning and sterilization procedures become easier. By releasing the tension on the ropes, the blood and tissue infiltrated amongst the strands of the ropes can be more easily removed. In addition, areas of contact between the ropes and other mechanical elements (like pulleys, end-effector links 8, 9, 10 or rotating elements 14, 15, 16) can be more easily accessed.

While this invention has been shown and described with reference to particular embodiments thereof, it will be understood by those skilled in the art that various changes in form and details may be made therein without departing from the spirit and scope of the invention as defined by the appended claims. For instance, the external tube 2' can be made out of different parts and can be attached to the proximal hub 4. In another embodiment, the internal structural element 2" can also be composed of different parts and can assume different geometries with diverse cross sections, namely tubular (with openings) or U-shaped.

It will also be easily understood by one of skill in the art that the invention can easily be deployed in the context of other micro-manipulation tasks where complex instruments are used, but regular cleaning and/or sterilization of internal elements of an instrument shaft is desirable. Solely by way of example, micro-manipulation tasks are performed in contaminated environments, wherein thorough cleaning of instrument elements is required after each use. In this context, a detachable outer shaft allowing access to internal elements may be desirable.

The invention claimed is:

1. A reusable surgical instrument comprising:
an articulated end-effector, mounted on a distal extremity of the reusable surgical instrument, comprising one or more end-effector links;
a proximal hub mounted on a proximal extremity of the reusable instrument configured to actuate the end-effector links;
mechanical transmission elements configured to transmit motion from the proximal hub to the articulated end-effector; and
a shaft which defines the longitudinal axis of the instrument, the shaft comprising one or more internal structural elements incorporating the mechanical transmission elements and an external tube having a threaded surface, the external tube configured to, when attached via the threaded surface, protect the one or more internal structural elements and prevent the passage of air through the reusable instrument to maintain insufflation of a body cavity and, when dis-attached via the threaded surface, expose the mechanical transmission elements from a corresponding threaded surface to a distal end of the shaft, wherein the one or more internal structural elements remain coupled to the proximal hub when the external tube is dis-attached.

2. The reusable surgical instrument of claim 1, wherein the external tube is configured to be dis-attached from the internal structural elements via the threaded surface and the corresponding threaded surface.

3. The reusable surgical instrument of claim 2, wherein the external tube is configured to be dis-attached from the internal structural elements via the threaded surface and the corresponding threaded surface without the need to disassemble any other components of the reusable surgical instrument.

4. The reusable surgical instrument of claim 2, wherein the external tube is configured to be re-attached to the internal structural elements via the threaded surface and the corresponding surface after a cleaning or sterilization procedure is performed on the instrument.

5. The reusable surgical instrument of claim 2, wherein at least one transversal element is mounted on the one or more internal structural elements to improve the air-tightness of the reusable instrument.

6. The reusable surgical instrument of claim 5, wherein the at least one transversal element comprises one or more small channels through which the mechanical transmission elements can pass.

7. The reusable surgical instrument of claim 6, wherein the external tube is in contact with at least one sealing element, which fills a gap between an internal surface of the external tube and the transversal elements.

8. The reusable surgical instrument of claim 1, wherein the external tube is configured to be dis-attached from over the internal structural elements and re-attached to over the internal structural elements via the threaded surface and the corresponding threaded surface for multiple use cycles of the instrument.

9. The reusable surgical instrument according to claim 1, wherein the external tube is in contact with at least one sealing element, which fills a gap between an internal surface of the external tube and the internal structural element.

10. The reusable surgical instrument according to claim 1, wherein the mechanical transmission elements comprise flexible mechanical elements, selected from the group consisting of wires, chains, ropes and belts.

11. The reusable surgical instrument of claim 10, wherein tension on the mechanical transmission elements is configured to be released after use to facilitate effective cleaning and sterilization procedures.

12. The reusable surgical instrument of claim 1, wherein the proximal hub comprises one or more rotating elements configured to actuate the end-effector links.

* * * * *